US 11,754,416 B2

(12) United States Patent
Uyeki et al.

(10) Patent No.: US 11,754,416 B2
(45) Date of Patent: Sep. 12, 2023

(54) SYSTEM AND METHOD FOR OPTIMIZED PAIRING OF PERSONAL TRANSPORT DEVICE TO RIDER

(71) Applicant: Honda Motor Co., Ltd., Tokyo (JP)

(72) Inventors: Robert Uyeki, Torrance, CA (US); Peter Wendt, Redondo Beach, CA (US); Matthew Staal, Torrance, CA (US); David Cun, Fountain Valley, CA (US)

(73) Assignee: Honda Motor Co., Ltd., Tokyo (JP)

( * ) Notice: Subject to any disclaimer, the term of this patent is extended or adjusted under 35 U.S.C. 154(b) by 114 days.

(21) Appl. No.: 16/915,311

(22) Filed: Jun. 29, 2020

(65) Prior Publication Data
US 2021/0404837 A1 Dec. 30, 2021

(51) Int. Cl.
*G01C 21/36* (2006.01)
*G01C 21/34* (2006.01)
*A61B 5/107* (2006.01)

(52) U.S. Cl.
CPC ..... *G01C 21/3679* (2013.01); *G01C 21/3407* (2013.01); *A61B 5/1072* (2013.01); *A61B 2503/12* (2013.01)

(58) Field of Classification Search
CPC ............ G01C 21/3679; G01C 21/3407; A61B 5/1072; A61B 2503/12
See application file for complete search history.

(56) References Cited

U.S. PATENT DOCUMENTS

| 7,976,433 | B2 | 7/2011 | Kenyon |
| 8,694,328 | B1 | 4/2014 | Gormley |
| 11,015,952 | B1* | 5/2021 | Lyle ..................... G01C 21/367 |
| 2002/0128933 | A1 | 9/2002 | Day et al. |
| 2007/0003910 | A1 | 1/2007 | Kirila |
| 2010/0306160 | A1 | 12/2010 | Simms |
| 2016/0334797 | A1* | 11/2016 | Ross ..................... H05K 999/99 |
| 2017/0011324 | A1* | 1/2017 | Truong .......... G06Q 10/063112 |
| 2018/0293911 | A1* | 10/2018 | Rastegar-Panah ..... G16H 50/20 |
| 2019/0171988 | A1* | 6/2019 | Kwatra .................. G06N 20/00 |
| 2019/0375301 | A1* | 12/2019 | Whitt .................... B60W 10/20 |
| 2019/0376802 | A1* | 12/2019 | Whitt ..................... G07C 5/008 |

(Continued)

FOREIGN PATENT DOCUMENTS

| CN | 109191203 A | 1/2019 |
| EP | 1134686 A1 | 9/2001 |

(Continued)

OTHER PUBLICATIONS

Espacenet Machine Translation of CN Patent No. 109191203 A.

(Continued)

*Primary Examiner* — Faris S Almatrahi
*Assistant Examiner* — Abdalla A Khaled
(74) *Attorney, Agent, or Firm* — Plumsea Law Group, LLC (57) ABSTRACT

A system and method for pairing a rider to a suitable electric transport device based on a variety of input parameters is described. The system involves a service provider that deploys at least two differently configured electric transport devices, and processes inputs from a user/rider such as biometric data, the rider's physical characteristics, rider experience level and preferences to pair the rider to a suitable electric transport device based on the inputs.

18 Claims, 7 Drawing Sheets

(56) References Cited

U.S. PATENT DOCUMENTS

| | | | |
|---|---|---|---|
| 2019/0384874 A1 | 12/2019 | Riley et al. | |
| 2020/0109956 A1* | 4/2020 | Nakamura | G01C 21/3476 |
| 2020/0124430 A1* | 4/2020 | Bradlow | G06Q 30/0207 |
| 2020/0149903 A1* | 5/2020 | Beaurepaire | G01C 21/3423 |
| 2020/0244744 A1* | 7/2020 | Xu | G06Q 10/02 |
| 2020/0309551 A1* | 10/2020 | Yang | G07C 9/00 |
| 2021/0102814 A1* | 4/2021 | Spielman | G06Q 10/02 |
| 2021/0155153 A1* | 5/2021 | Wendt | G08G 1/096725 |
| 2021/0182751 A1* | 6/2021 | Pan | G06F 3/04883 |
| 2021/0286651 A1* | 9/2021 | Ho | G06F 3/0608 |
| 2021/0302174 A1* | 9/2021 | Abdulla | G06Q 30/0645 |

FOREIGN PATENT DOCUMENTS

| | | |
|---|---|---|
| EP | 2535248 B1 | 12/2016 |
| JP | 2019091370 A | 6/2019 |
| KR | 20110127957 A | 11/2011 |

OTHER PUBLICATIONS

Espacenet Machine Translation of Published JP Application No. 2019091370 A.

Espacenet Machine Translation of the Abstract of Published KR Application No. 20110127957 A.

\* cited by examiner

FIG. 1

SYSTEM AND METHOD FOR OPTIMIZED PAIRING OF PERSONAL TRANSPORT DEVICE TO RIDER

CROSS-REFERENCE TO COMMONLY OWNED APPLICATION(S)

The disclosure of co-pending application Ser. No. 16/836,802 filed Mar. 31, 2020, is hereby incorporated by reference in its entirety.

BACKGROUND

This disclosure relates generally to mobility, and in particular to a system and method for optimizing a pairing of a rider to an electric personal transport device based on criteria such as a rider's physical characteristics and other factors such as riding experience, tendencies and preferences.

With rising prices of gasoline and automobiles, many people may turn to other more cost efficient modes of transportation such as, for example, mopeds, bicycles, scooters and, more recently, electric personal transport devices such as stand-up electric scooters or kick scooters. These personal transport devices may be particularly popular for shorter trips in a city environment due to their compact size, ease of use, mobility, and the fact that they may be folded as needed for ease of portability. They may also be useful for covering the proverbial first mile or last mile of a trip which is the link between a user's origin or destination and another transportation means, hub or mass transit network.

As electric personal transport devices become more commonplace, there is a recognition that riders come in many sizes, with varying physical characteristics that may be accommodated, and with varying levels of ridership experience. While most personal transport devices are deployed using a single configuration or size, there may be an increasing demand for deploying multiple configurations to match with riders' physical characteristics, needs and/or experience.

SUMMARY

A system and method for pairing a rider or user to a suitable electric transport device is disclosed. The system and method rely on inputs from the user regarding parameters such as biometric data, physical characteristics such as any limitations or restrictions, rider experience level and preferences and determines a suitable matched device based on the input parameters. The service provider renting the electric transport devices may provide at least two differently configured devices which are paired to a user based on their input parameters and details.

In one aspect of the disclosure, a system for pairing a user to an electric transport device suitable for the user is described. The system comprises a plurality of electric transport devices including at least a first type of device, and a second type of device configured differently from the first type of device. The system also includes a service provider deploying and tracking the plurality of electric transport devices, the service provider including at least one processor executing the instructions to receive a request to initiate a ride of an electric transport device, receive input regarding a user's physical characteristics, and pair the user to a suitable electric transport device based on the user's physical characteristics. In pairing the user to the suitable device, the system will select from among the first type of device and the second type of device, and then direct the user to the paired suitable electric transport device to initiate the ride.

In another aspect of the disclosure, a system for pairing a user to an electric transport device suitable for the user is described in which the system includes a plurality of electric transport devices comprising a first type of device, and a second type of device configured differently from the first type of device, and a service provider deploying and tracking the plurality of electric transport devices, the service provider including at least one processor. The processor executes the instructions to receive a request to initiate a ride of an electric transport device, receive input regarding a user's physical characteristics, and receive input regarding a user's preferences. The system pairs the user to a suitable electric transport device based on the user's physical characteristics and preferences selected from among the first type of device and the second type of device, and then directs the user to the paired suitable electric transport device to initiate the ride.

In another aspect of the disclosure, a method for pairing a user to a suitable electric transport device from among a plurality of types of electric transport devices is described in which the method includes the steps of receiving a request from a user to initiate a ride, receiving input regarding the user's physical characteristics, and pairing the user to a suitable electric transport device based on the user's physical characteristics selected from among the plurality of types of devices. The method includes the step of directing the user to the paired suitable electric transport device to initiate the ride.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like reference numerals designate corresponding parts throughout the different views.

DETAILED DESCRIPTION

Systems and methods for optimizing the pairing of a user to a suitable electric transport device are described herein. The techniques of the present embodiments may be used to allow users of electric transport devices to input user characteristics such as biometrics, physical restrictions, rider preferences and rider experience to optimize the pairing of a suitable electric transport device to the user.

The example embodiments are described herein with reference to an electric transport device in the form of an electric scooter. As used herein, an electric scooter is a term used mainly to describe a stand-up kick scooter that is electrically powered. For example, this is a type of personal transport device that is gaining ridership in many locations. The principles of the example embodiments described herein may be applied to electric scooters or other types of electric transport devices, such as bicycles, unicycles, mopeds, skateboards, kickboards, wheelchairs, personal transporters, or the like. The electric transport devices may also allow for multiple riders or cargo transport.

The present embodiments allow for an electric scooter rental platform which includes more than one type of scooter, that is, availability of differently configured scooters such as different form factors and/or sizes which may be paired with a rider based on a rider's physical characteristics and possibly other factors such as riding experience, tendencies and preferences. The physical characteristics may include a rider's height and weight to optimize pairing of the rider with a scooter of an appropriate size and scale. Physical characteristics may also include physical restrictions or limitations such as a need to ride in a seated position instead of a standing position, or the need for assisted balance. Multiple other factors may be input to further optimize pairing the rider to a suitable scooter, for immediate rental or for reservation at a particular location. Rider preferences such as providing space for cargo or multiple passengers may also be accommodated.

Figure 1:
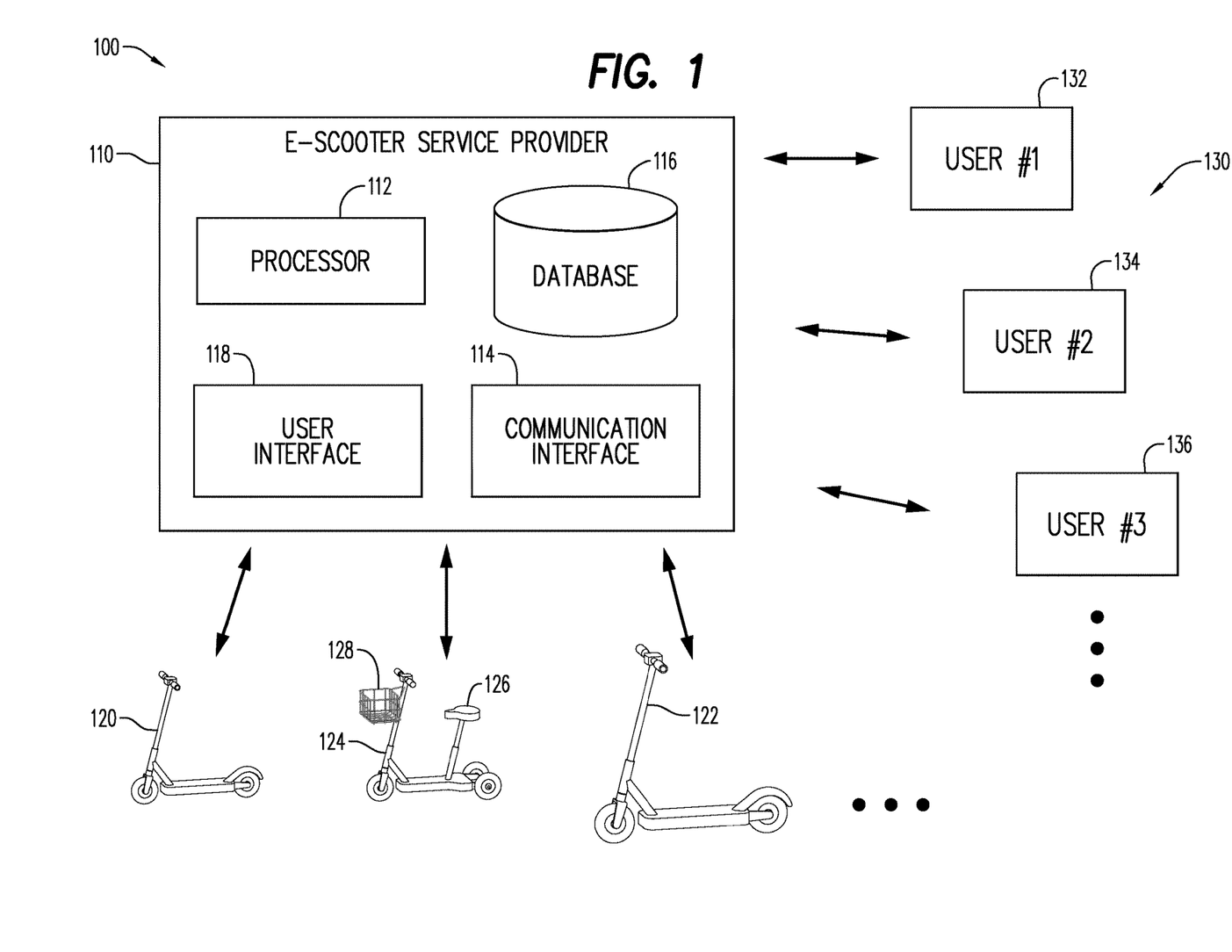
FIG. 1 is a block diagram of an example embodiment of an electric transport device service provider system in accordance with aspects of the present disclosure.

Referring now to FIG. 1, a block diagram of a system 100 for optimized pairing of a rider to a suitable electric transport device is shown. In an example embodiment, the system 100 may include an electric scooter or "e-scooters" service provider 110 (also referred to herein as "service provider 110") for providing rentals of electric transport devices to users. In an example embodiment, the service provider 110 may rent one or more different types of electric transport devices, such as electric scooters, to users for personal transportation from a location to a destination. In the example embodiments, the service provider 110 may provide e-scooter rentals to users, however, it should be understood that service provider 110 may offer any type of electric transport device for rental to users.

In this embodiment, the service provider 110 may include at least a processor 112 that is in communication with a communication interface 114, a database 116, and a user interface 118. In some embodiments, the processor 112 may be a dedicated central processing unit (CPU) configured to implement the techniques described herein. In other embodiments, the processor 112 may be any computer or computing system, including, but not limited to configurations having multiple processors, one or more servers, and/or a distributed computing system that is located remotely from the service provider 110.

In an example embodiment, the system 100 may also include a plurality of electric transport devices of different configurations. In the illustration, an electric transport device 120 is configured as a stand-up kick scooter, a differently configured electric transport device 122 is a stand-up kick scooter of larger scale, and still another differently configured electric transport device 124 is a scooter with a seat 126 and a stowage area 128. While the illustrated device shows a stowage area 128 which is a basket or the like, it is contemplated that other configurations of stowage area are possible such as an area on the platform with tie downs, or even an auxiliary device such as a side car that attaches or is pulled by the device.

The device 124 may also be configured with three wheels instead of two for stability particularly for riders that may want assistance with balance. The configurations in the illustration are exemplary, and one of ordinary skill in the art would understand that a variety of configurations and combinations of features are contemplated. The system 100 would include at least two different configurations to pair a user with a suitable type based on the user's physical characteristics, preferences or experience.

For example, a plurality of differently configured electric transport devices 120, 122 and 124 may be located at various locations throughout a geographic area where there is a high density of users of electric transport devices, such as cities and other urban type environments. As shown in FIG. 1, the system 100 may include a plurality of users 130. In this embodiment, the plurality of users 130 may include at least a first user 132, a second user 134, and a third user 136. In other embodiments, the system 100 may include any number of users. In an example embodiment, the service provider 110 may include components embodied in hardware, software, or a combination thereof that are configured to implement the techniques described herein for synchronizing the start of group ride rentals of electric transport devices for users.

In an example embodiment, the communication interface 114 may be configured to enable various wireless network communications, such as via code division multiple access (CDMA) and/or global system for mobile communications (GSM) networks, as well as one or more of Bluetooth, WiFi, and/or other wireless communication technologies, including short-range wireless, ultra-wideband, or near-field communication technologies. In this embodiment, the communication interface 114 may be configured to allow the service provider 110 to communicate with other components of the system 100, including one or more of plurality of electric transport devices 120 and/or a central monitoring system (not shown). For example, in one embodiment, the communication interface 114 may be a wireless transceiver that transmits and/or receives signals (e.g., commands, messages, information, etc.) to and/or from one or more of the plurality of electric transport devices 120 and one or more of the plurality of users 130, as well as the central monitoring system.

In some embodiments, the service provider 110 may also include a database 116 that includes information associated with one or more of plurality of users 130 and/or plurality of electric transport devices 120, 122 or 124. For example, the database 116 may include user or account information, such as usernames and passwords, billing information, etc. Linked to the user or account information database 116 may also include user profile information stored in a memory regarding a user's physical characteristics, preferences, and experience. The database 116 may also include information associated with the one or more plurality of electric transport devices 120, 122 or 124 in the geographic area associated with the service provider 110. For example, the database 116 may include identification information about each of the plurality of electric transport devices, including the details of the e-scooter 122, the details of the e-scooter 124, and/or the details of the e-scooter 126, such as a serial number or identifier, as well as other information, including, but not limited to a state of charge or battery status, usage data (e.g., miles, hours of service, etc.), device type or model, device size or scale, rider position, stowage, or any other information that may be used by the service provider 110.

The database 116 may include details about the scooters that include the configuration parameters that may correlate with the parameters input about the user such as rider size, and other biometric information, driver assist technologies that correlate to a user's physical characteristics or limitations that may make one type of scooter preferred over another type of scooter for the user.

The device information in the database may also include configuration parameters that correlate to the inputs regarding rider experience and rider preferences that may make one type of scooter preferred over another type of scooter for the particular user. It will be understood that the service provider may use any suitable correlation process to match a user to a suitable scooter configuration that is available based on the user inputs. All types of devices available in the system would be indexed or correlated to particular user inputs to provide an optimal match of user to device.

In this embodiment, the service provider 110 also includes the user interface 118 that is configured to allow a user, for example, one or more of plurality of users 130, including a first user 132, a second user 134, and/or a third user 136, to interact with the service provider 110. In one embodiment, the user interface 118 may be configured to interact with a user through a mobile device, such as a smart phone or tablet, using short-range communication technologies, such as, Bluetooth®. In an example, a user may interact with the user interface 118 of the service provider 110 through an application (also referred to as an "app") on the user's mobile device.

In an exemplary embodiment, the electric transport devices or e-scooters 120, 122 and 124 may include a dock or other apparatus for receiving a mobile device, such as a smart phone or other type of portable computing device, associated with a user of the e-scooter. With an application installed on the user's mobile device, the mobile device may function as a display screen for the electric transport device or e-scooter and provides a communication interface to an onboard controller or processor of the electric transport device (if present), as well as allowing communication with the communication interface 114 and/or the user interface 118 of service provider 110.

As described above, communication between the user's mobile device and the onboard controller or processor of the e-scooter 120, for example, as well as with the communication interface 114 and/or the user interface 118, may be accomplished by a variety of ways such as Bluetooth® or other types of short-range wireless or near-field communication protocols. The display screen of the mobile device may provide information to the user of the electric transport device regarding, for example, battery life, status of lighting units, distance traveled, speed, navigation information, hazard information and roadway infrastructure signals and readings. The application on the mobile device may also monitor and/or control some of the operating systems of the electric transport device. For example, information associated with braking, speed, location, heading, turn status, etc. may be monitored and/or controlled via the application on the mobile device.

Figure 2:
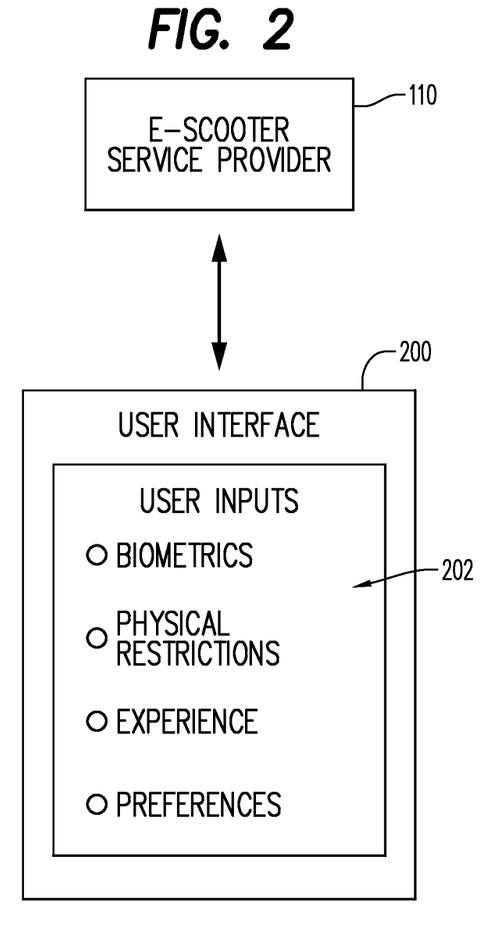
FIG. 2 is a representative view of an illustrative user interface for inputting a user's physical characteristics, experience or preferences for pairing with a suitable electric transport device in accordance with aspects of the present disclosure.

Referring now to FIG. 2, a representative view of a user interface 200 for pairing a user to a suitably configured electric transport devices is shown. As described above, in some embodiments, a user (e.g., one or more of plurality of users 130) may interact with user interface 118 of service provider 110, for example, through an application or website, to rent one or more of plurality of electric transport devices 120. In an example embodiment, the user interface 200 may be provided on the user-side, for example, through a user's mobile device, such as mobile telephone, tablet, computer, or other device, to allow the user to initiate a group ride rental with the service provider 110 for multiple users of the plurality of electric transport devices 120.

In this embodiment, the user interface 200 may include inputs 202 which are parameters for pairing a user to a suitable electric transport device. The parameters may include, but are limited to, a user's biometrics, physical restrictions, riding experience and other preferences. These inputs 202 may be selected or input by the user when initiating a ride, or may be stored from previous rides in the user's account or profile. With this arrangement, any user may be provided the option of storing their input factors in their account or profile with service provider 110 so that they are paired with a suitable device in future transactions.

Figure 3:
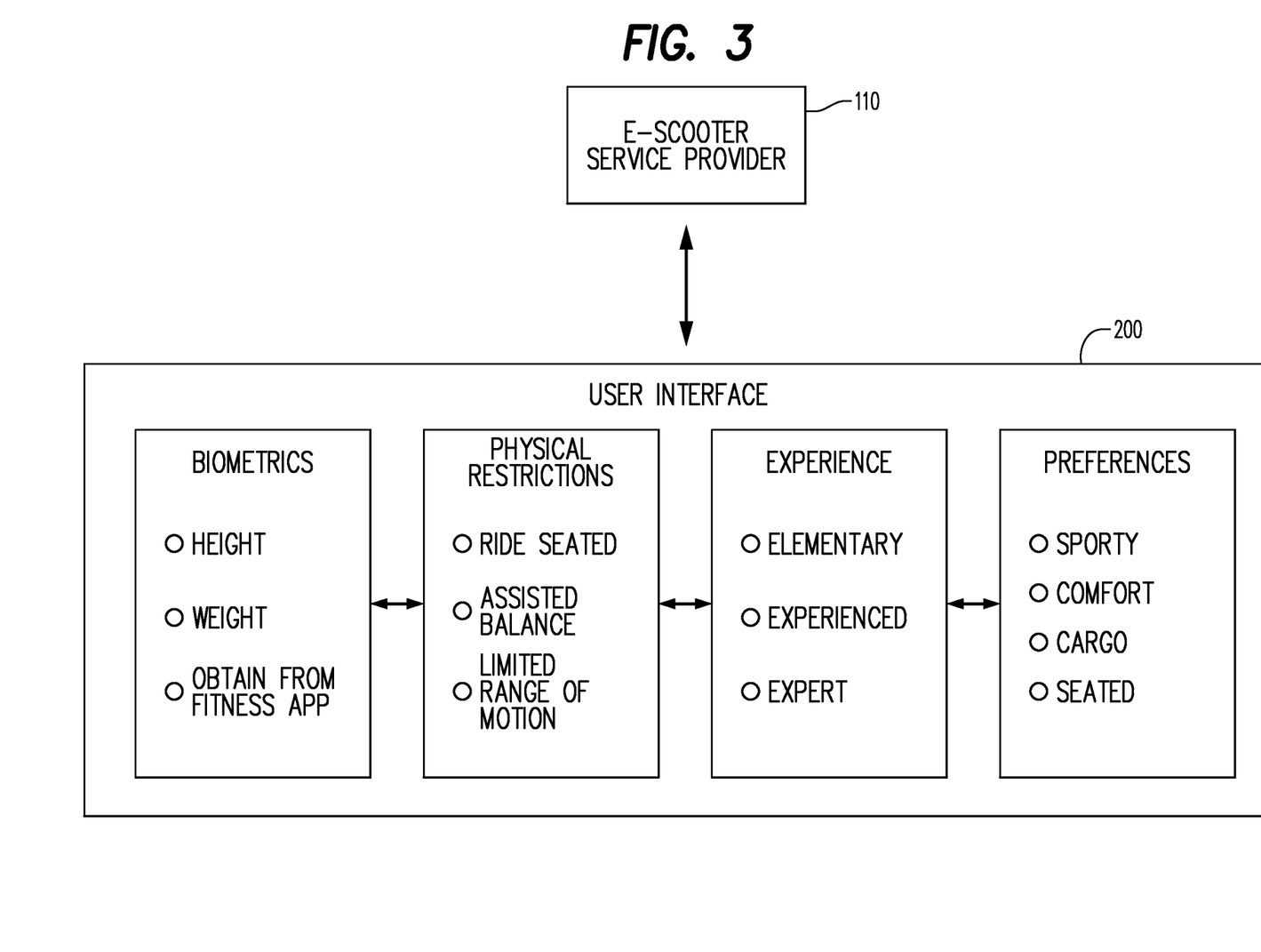
FIG. 3 is a representative view of an illustrative user interface for selecting or inputting the user inputs for pairing with a suitable electric transport device in accordance with aspects of the present disclosure.

Referring now to FIG. 3, a representative view of the user interface 200 with a more detailed view of how the parameters may be defined with parameter details is shown. As for a user's biometrics, information about a user's size such as a user's height and weight may be input when initiating a ride, or retrieved from their profile. A user's size may be used to select a suitable device as the differing configurations may include scale and robustness of a scooter. Details about the user's biometrics may also be obtained from a health tracking or fitness app that the user already uses and for which the user gives consent for the data to be shared with service provider 110.

For the biometric parameter, the service provider 110 may determine that height may be a determining characteristic for recommending a scooter configuration. Customarily when a user is standing on the scooter deck, the scooter bar should be around the hip to waist height of the user an optimal balance of comfort, control and performance. If the bar is too far above the waist or too far below the hip, the rider may find the hand position uncomfortable and awkward. In this example, the scooter 120 may be determined to be a best fit for a user whose height is between 60 inches and 72 inches, while the scooter 122 may be determined to be a best fit for a user whose height exceeds 72 inches. Any appropriate indexing or coding method may be employed to categorize scooters according to a user's height input. The scale of the scooter also entails the size of the scooter deck which may be proportionally scaled to a rider's size.

Alternatively for the biometric parameter, the service provider 110 may determine a rider's weight to be a determining characteristic for recommending a scooter configuration. Again in this example, the scooter 120 may be determined to be a best fit for a rider whose weight is under a predetermined limit, and the scooter 122 may be determined to be a best fit for a rider whose weight exceeds the predetermined limit. Any appropriate indexing or coding method may be employed to categorize scooters according to a user's weight input. It is possible that the handle bar may be height adjustable such that a rider who may be heavy for their height based on a height to weight table in the database 116 may be paired with the scooter 122 for best fit for weight and allow for handle height adjustment.

As for the physical characteristics parameter, the user may be provided with options such as the need to ride in a seated position as opposed to standing, need assistance with balance, and any limited range of motion, for example. Each of these parameter details may be used by the service provider to pair the user with a suitable device. For example, if the user selected "ride seated" or the like, a resulting matched scooter may be one that includes a seat. In another example, if the user selected "assisted balance" or the like, a resulting paired scooter may one that is configured with three or four wheels that does not require the user to balance on two wheels. If the user selected "limited range of motion" or the like, a resulting matched scooter may be one that includes a steering assist or other assisted riding technology. The configuration details may be coded to each scooter in the database 116 to enable processing the user inputs to match with a suitably configured scooter.

As for the experience parameter, the user may be provided with options such as elementary or beginning rider, experienced, or expert level rider. Each of these parameter details may be used by the service provider to pair the user to a suitable device. For example, if the selected experience parameter is "elementary" or the like, a resulting matched scooter may be one that includes balance assistance, three or four wheels for easier handling or a speed limiter. The scooters in the service provider's fleet may also be coded according to deck size since a larger deck may generally be easier to maneuver particularly for an inexperienced rider. The number of wheels may be a determining factor for balance assistance or inexperienced riders.

If the user selected "experienced" or the like, a resulting matched scooter may be one selected from a wider range of configurations since an experienced rider may be able to handle many types of devices. The service provider 110 may have more leeway to recommend various configurations to experienced or expert riders than with elementary or beginner riders. The experienced riders may generally be steered toward two-wheeled scooters and may include proportionally shorter decks for maneuverability.

As another example, if the user selected "expert" or the like, a resulting matched scooter may be one that is configured for advanced maneuverability or speed. A shorter deck may generally be a factor for advanced maneuverability for an expert rider, as well as a lower handle bar configuration.

In this manner, the service provider 110 may predetermine features of a scooter that correlate to particular experience parameters and may store this information for each scooter in the database 116. The correlation may be accomplished in a variety of possible ways such as assigning an experience parameter value symbolizing an experience level to each scooter, and matching same to a corresponding user experience level as input into the user interface 118. Any suitable scheme of assigning an experience parameter to each scooter and comparing with user input to determine a best fit may be employed. Alternatively, the user interface 118 may prompt the user for comments or responses which may then be employed to compare with scooters based on their experience parameter values and thereby determine a best fit for any given user.

As for the preferences parameter, the user may be provided an array of options such as, but not limited to, a sporty ride, a comfort ride, the need to carry cargo or a preference to ride in a seated position. For example, if the user selected "sporty" or the like, a resulting paired scooter may be one that is configured for advanced maneuverability or speed or road feel. If the user selected "comfort" or the like, a resulting paired scooter may be one that is configured with a wider base, with a smoother ride, or include a seated riding position. If the user selected "cargo" or the like, a resulting paired scooter may be one configured with an area for loading a parcel or bag such as a basket or a cargo hold and tie downs or a cover. If the user selected "seated" or the like, a resulting paired scooter may be one configured with a seat. More preferences than those illustrated in FIG. 3 are contemplated. For example, one preference may be for more than one rider to initiate a ride together, or may be for a defined geographic area. Any number of preferences are possible for the service provider to include in the pairing process.

It is contemplated that each of the parameters described, and each of the parameter details or options, may be used alone or in combination with other options and parameters to determine a suitable configuration of a resulting matched device. Some parameters and parameter details may provide an overlapping set of criteria in the pairing criteria. It is also contemplated that a service provider may develop a priority grouping of parameters such as essential and optional, or develop a hierarchy of parameters ranging in importance in order to make the determination of a suitable electric transport device configuration for any given user. As described above with respect to the experience parameter, it is also contemplated that a service provider may develop a system of assigning values for each parameters and parameter details and storing such values for each scooter in the database 116. In this manner, each scooter may be assigned various values for a set of parameters which may be employed to match a user to a suitable scooter based on the inputs for the user.

An example of overlapping set of criteria is a user whose weight exceeds a predetermined threshold and inputs they are an experienced rider with a parcel to stow. These factors would be input into the system and a suitable device may be a scooter configured like the scooter 122 for strength, with two wheels due to the rider's experience and with a basket 128 provided for the parcel.

Another example may be a user whose weight is below the predetermined threshold, and whose height is below 72 inches. This user may indicate a preference to ride in a seated position but also indicate expert level. The resulting paired scooter for this rider may resemble the scooter 125 shown in FIG. 4. The scooter 125 with two wheels may provide greater maneuverability for an experienced rider.

Various permutations of the parameters described herein are possible and contemplated and may be dependent upon the number of configurations in a service provider's fleet of devices.

Figure 4:
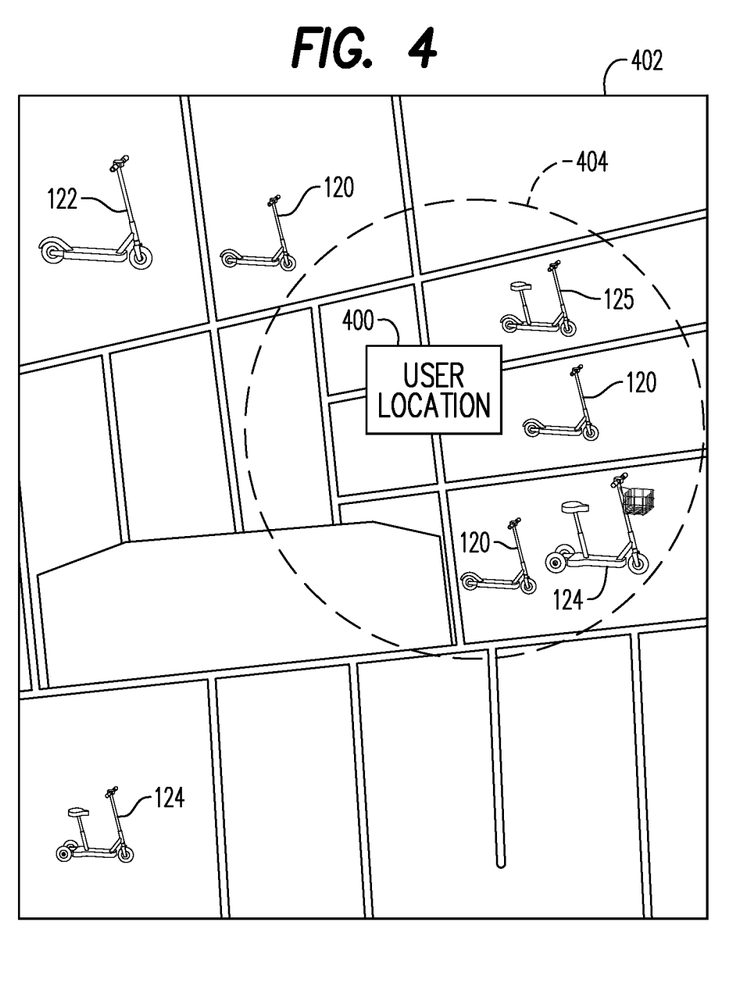
FIG. 4 is a schematic view of an example embodiment of a user location with variously configured electric transport devices in proximity in accordance with aspects of the present disclosure.

FIG. 4 is a schematic view of an example embodiment of pairing a suitably configured electric transport device for a user at an exemplary rental location. As described above, in some embodiments, a user would input or load the parameters discussed above, and the service provider pairs or matches the user to an electric transport device nearby that is suitable based on the parameters. As shown in FIG. 4, a user which may be any one of users 130, is located at a user location 400 from which the user initiates a rental. In some embodiments, a map 402 of the geographic area in which the user is located at the user location 400 may be displayed on the user's mobile device, for example, through user interface 200 of the application running on the mobile device of the user. In an example embodiment, the map 402 may include icons or other indicia to designate the location of one or more electric transport devices within the geographic area shown on the map 402. In an example embodiment, the map 402 may include a predetermined area 404 centered around the user location which contains the closest devices.

For example, as shown in FIG. 4, the predetermined area 404 is approximately a circular area having a radius centered on the user location 400 and extending outward a set distance. The predetermined area 404 may be approximately 2-3 blocks or may be determined using other proximity criteria, such as time (e.g., within a 5-10 minute walk from user location 400) or distance in miles or kilometers (e.g., ¼ mile or less from user location 400). Other criteria may also be used in addition to, or alternatively, to show the available electric transport devices that may be rented. The map may display the various configurations or types of electric transport devices available for rent based on the user's input parameters. In this exemplary illustration, a two-wheeled scooter 120 is shown, as is a larger scale two-wheeled scooter 122, a three-wheeled scooter 124 with a seat 126 and basket 128, and a two-wheeled scooter with seat 125. These examples are simply illustrative of the various configurations which may be offered by a service provider, and other permutations of the features are possible. The principles of the embodiments can be carried out with just two different configurations of devices which may be paired with users inputting suitable characteristics.

In this embodiment, a user at the user location 400 has input their characteristics and at least four electric transport devices are within predetermined area 404. Of these configurations, the service provider 110 may match or pair the user with a suitable device according to the various parameters and options input into the system. The suitable device may depend on the parameters and characteristics and the process implemented by the service provider of employing the parameters to determine a best fit. Once a suitable device is determined and selected, the user would choose and complete the rental process to initiate the ride.

In some embodiments, electric transport devices may be in a locked state prior to rental by a user. In this locked state, the electric motor and/or wheels of the electric transport device may be disabled or prohibited from moving so that the electric transport device is not functional by either powered or manual operation.

Figure 5:
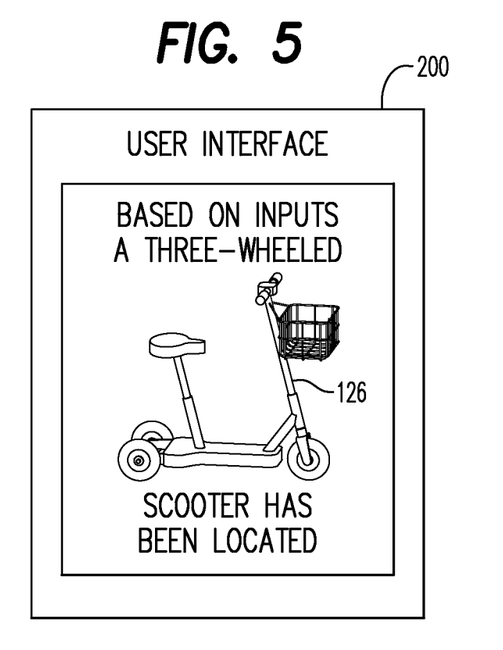
FIG. 5 is a representative view of an illustrative user interface for informing the user of a suitable electric transport device paired to the user in accordance with aspects of the present disclosure.

Referring now to FIG. 5, a representative view of the user interface 200 for displaying a recommended resulting electric transport device is shown. In this illustrative example, the parameters and options input by the user resulted in a pairing with scooter 126 having three wheels, a seated riding configuration and a basket for stowage. User interface 200 may be configured to enable the user to confirm the paired scooter configuration in a known way such as tapping to confirm or tapping a graphical user interface (not shown).

Figure 6:
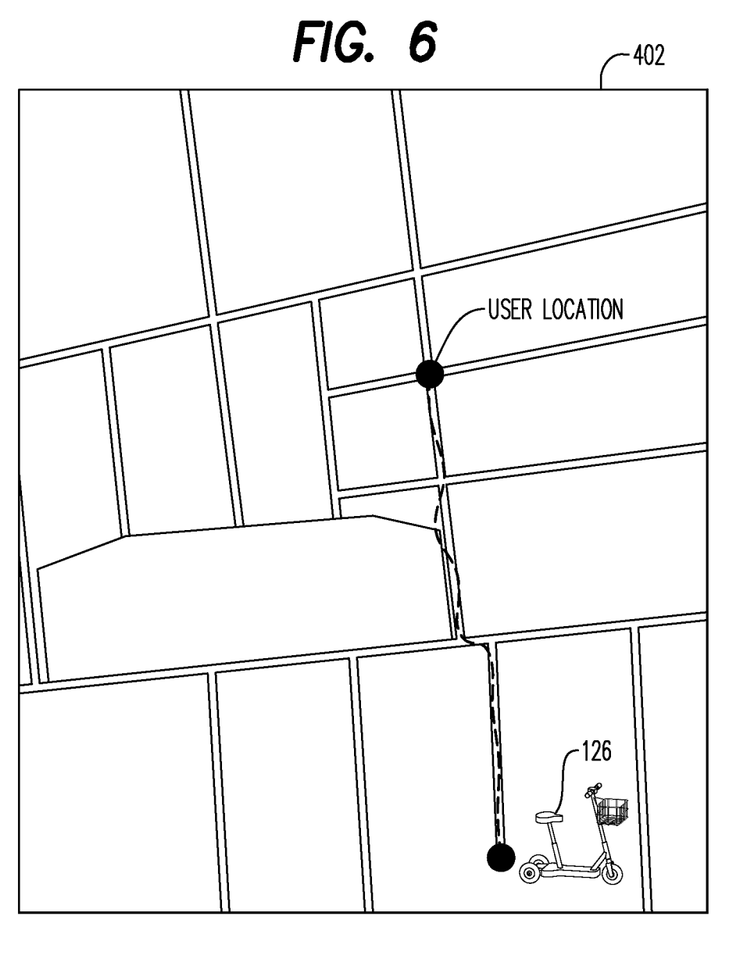
FIG. 6 is a schematic view of an example embodiment of guiding the user to the paired electric transport device in accordance with aspects of the present disclosure.

FIG. 6 is a schematic view of an example embodiment of a user locating an electric transport device from their location. This display may include a map 402 that guides the user to paired scooter 126. FIG. 6 illustrates the guidance on the map 402 similar to navigation tools that may be familiar to most users. The system may include verbal turn by turn verbal guidance in addition to the graphical map display. It is also possible that the map 402 may illustrate more than one suitable device which the user may select on the map. In other words, a number of suitable devices may be within the predetermined area 404 which may be defined to be within a reasonable walking distance from the user location. It is understood that a user may have factors other than distance from user location which may make one location preferred over another such as proximity to their final destination, or proximity to another desired stop or feature such as a landmark or meeting point. The map 402 may provide multiple options of suitably paired scooters for the user to select.

Figure 7:
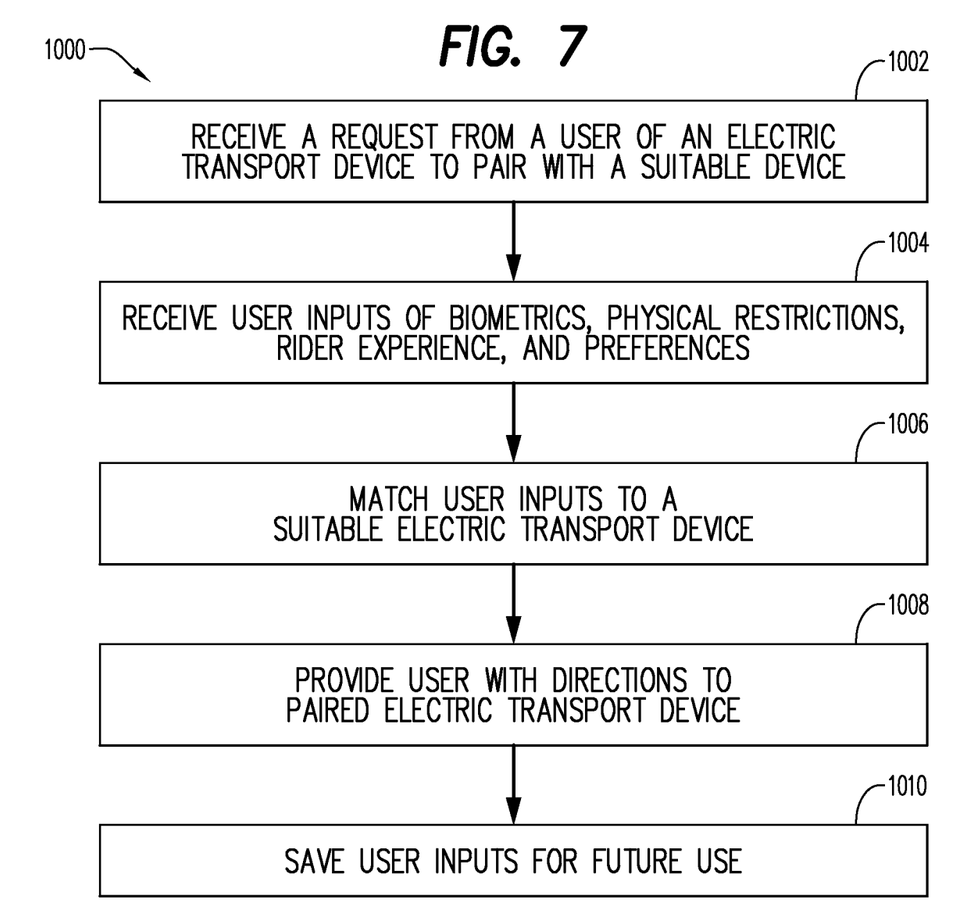
FIG. 7 is a flowchart of an exemplary method for pairing an electric transport device to a user in accordance with aspects of the present disclosure.

FIG. 7 is a flowchart of a method 1000 for pairing a user to a suitable electric transport device according to an example embodiment. In some embodiments, the method 1000 may be implemented by a computer or processor associated with an electric transport device service provider, for example, the service provider 110, described above. In an example embodiment, the method 1000 may begin with an operation 1002. At operation 1002, a request may be received from a user of an electric transport device to initiate a ride. For example, at operation 1002, the first user 132 may interact with the service provider 110 using they option 202 on the user interface 200 to initiate a ride.

Next, at an operation 1004, method 1000 may include inputting parameters such as biometrics, physical restrictions, rider experience, and preferences. As described heretofore, each of these parameters may include multiple details and options. At an operation 1006, the service provider 110 may match a user with a suitable electric transport device based on the parameters and details input into the system. At operation 1008, the user may be provided with directions to the paired electric transport device to initiate the rental. Optionally, at operation 1010, the user interface 200 may prompt the user to confirm whether the parameters input and details selected should be saved for future use in the user's profile. In this way, details such as a user's height and weight, and rider experience and preferences may be saved in the user's profile so that in a future rental, the parameters are already input or automatically input from the user profile. It is also contemplated that the user's biometrics in particular may be provided to the service provider from a health tracking or fitness app which the user already uses on the mobile device for example.

In addition to pairing one user to a suitable electric transport device, it is possible that the system could be used to reserve suitable devices for multiple users based on each user's parameters. The principles of the present disclosure may be employed to enable a plurality of users to input their respective parameters to be paired with a suitable device for each user. The resulting matched devices may be reserved for rental at a later time, and the principles of the group ride described in co-pending application Ser. No. 16/836,802 filed Mar. 31, 2020, may be employed with a suitable scooter paired to each user.

While the electric transport device illustrated and described in reference to the exemplary embodiments is as an electric scooter, any type of small, personal electric transport vehicle may be employed, including, but not limited to an electric skateboard, one- and two-wheeled self-balancing boards, electric bicycles or e-bikes, electric-assisted mopeds, small electric-powered mobility transporters, or any other type of personal transportation device, as described above.

While various embodiments of the disclosure have been described, the description is intended to be exemplary, rather than limiting and it will be apparent to those of ordinary skill in the art that many more embodiments and implementations are possible that are within the scope of the disclosure. Accordingly, the disclosure is not to be restricted except in light of the attached claims and their equivalents. Also, various modifications and changes may be made within the scope of the attached claims.

We claim:

1. A system for pairing a user to an electric transport device selected for the user, the system comprising:
 a plurality of electric transport devices comprising devices of a first type of device, and comprising devices of a second type of device configured differently from the first type of device; and a service provider deploying and tracking the plurality of electric transport devices, the service provider including at least one processor configured to:
  receive a request to initiate a ride of an electric transport device;
  identify a set of available electric transport devices present in a predetermined area based on proximity to the user, using an electronic map provided on a display of a mobile device of the user;
  receive input regarding an experience parameter corresponding to the riding expertise of the user;
  receive input regarding physical characteristics of the user;
  pair the user to a paired selected electric transport device based on the experience parameter of the user as a factor in selection of the paired selected electric transport device by comparing the experience parameter of the user to experience parameters assigned to corresponding electric transport devices, and the physical characteristics of the user, selected as one of the first type of device and the second type of device from the set of available electric transport devices;
  wherein the mobile device of the user is connected to the paired selected electric transport device using a dock;
  direct the user to the paired selected electric transport device to initiate the ride, using the electronic map;
  connect the mobile device of the user to the paired selected electric transport device; and
  control operating systems of the paired selected electric transport device using the mobile device of the user.

2. The system of claim 1, wherein the processor receives input regarding preferences of the user, and the pairing is based on the physical characteristics of the user and the preferences of the user.

3. The system of claim 1, wherein the electronic map shows icons corresponding to corresponding electric transport devices from the set of available electric transport devices and the icons show configuration information of the corresponding electric transport devices used to pair the user to the paired selected electric transport device based on the riding expertise of the user.

4. The system of claim 1, wherein the electronic map shows icons corresponding to corresponding electric transport devices from the set of available electric transport devices and the icons show configuration information of the corresponding electric transport devices used to pair the user to the paired selected electric transport device based on the physical characteristics of the user.

5. The system of claim 1, wherein the input regarding the physical characteristics of the user further comprises biometric information of the user including height information and the at least one processor is configured to pair the user with the paired selected electric transport device by selecting an electric transport device having a handle bar with a position selected based on the height information.

6. The system of claim 1, wherein the riding expertise is at least one of elementary and beginner and the paired selected electric transport device includes at least one of balance assistance features, a speed limiter, and a large deck.

7. The system of claim 1, wherein the input regarding the physical characteristics of the user further comprises a requirement for the user to be seated while riding.

8. The system of claim 1, wherein the input regarding the physical characteristics of the user further comprises a requirement to assist with balancing and the paired selected electric transport device includes one of three wheels and four wheels.

9. The system of claim 2, wherein the riding expertise is at least one of experienced and expert and the paired selected electric transport device includes at least one of a two-wheeled configuration, a short deck, advanced maneuverability, advanced speed, and a low handle bar.

10. A system for pairing a user to an electric transport device selected for the user, the system comprising:
  a plurality of electric transport devices comprising devices of a first type of device, and comprising devices of a second type of device configured differently from the first type of device; and
  a service provider deploying and tracking the plurality of electric transport devices, the service provider including at least one processor configured to:
    receive a request to initiate a ride of an electric transport device;
    identify a set of available electric transport devices present in a predetermined area based on proximity to the user, using an electronic map provided on a display of a mobile device of the user;
    receive input regarding physical characteristics of the user, wherein the input regarding the physical characteristics of the user comprises at least one physical restriction of the user and the at least one physical restriction of the user comprises a requirement to be seated while riding;
    receive input regarding an experience parameter corresponding to a riding expertise of the user;
    receive input regarding preferences of the user;
    pair the user to a paired selected electric transport device, based on the physical characteristics of the user, the experience parameter of the user as a factor in selection of the paired selected electric transport device by comparing the experience parameter of the user to experience parameters assigned to corresponding electric transport devices, and the preferences of the user, selected as one of the first type of device and the second type of device from the set of available electric transport devices;
    wherein the paired selected electric transport device includes a seat;
    wherein the mobile device of the user is connected to the paired selected electric transport device using a dock;
    direct the user to the paired selected electric transport device to initiate the ride, using the electronic map;
    connect the mobile device of the user to the paired selected electric transport device; and
    control operating systems of the paired selected electric transport device using the mobile device of the user.

11. The system of claim 10, wherein the riding expertise is at least one of elementary and beginner and the paired selected electric transport device includes at least one of balance assistance features, a speed limiter, and a large deck.

12. The system of claim 10, wherein the riding expertise is at least one of experienced and expert and the paired selected electric transport device includes at least one of a two-wheeled configuration, a short deck, advanced maneuverability, advanced speed, and a low handle bar.

13. The system of claim 10, wherein the electronic map shows icons corresponding to corresponding electric transport devices from the set of available electric transport devices and the icons show configuration information of the corresponding electric transport devices used to pair the user to the paired selected electric transport device based on the riding expertise of the user.

14. The system of claim 10, wherein the configuration difference between the first type of device and the second type of device is a stowage area.

15. A method for pairing a user to a selected electric transport device from among a plurality of types of electric transport devices, the method comprising:
   receiving a request from the user to initiate a ride;
   identifying a set of available electric transport devices present in a predetermined area based on proximity to the user, using an electronic map provided on a display of a mobile device of the user;
   receiving input regarding physical characteristics of the user, wherein the input regarding the physical characteristics of the user comprises at least one physical restriction of the user and the at least one physical restriction of the user comprises a requirement to assist with balancing;
   receiving input regarding an experience parameter corresponding to a riding expertise of the user;
   pairing the user to a paired selected electric transport device based on the physical characteristics of the user and the experience parameter of the user as a factor in selection of the paired selected electric transport device by comparing the experience parameter of the user to experience parameters assigned to corresponding electric transport devices, selected from among the plurality of types of devices as one of the plurality of types of devices from the set of available electric transport devices;
   wherein the paired selected electric transport device includes one of three wheels and four wheels;
   wherein the mobile device of the user is connected to the paired selected electric transport device using a dock;
   directing the user to the paired selected electric transport device to initiate the ride, using the electronic map;
   connecting the mobile device of the user to the paired selected electric transport device; and
   controlling operating systems of the paired selected electric transport device using the mobile device of the user.

16. The method according to claim 15, wherein the riding expertise is at least one of elementary and beginner and the paired selected electric transport device includes at least one of a speed limiter and a large deck.

17. The method according to claim 15, wherein the electronic map shows icons corresponding to corresponding electric transport devices from the set of available electric transport devices and the icons show configuration information of the corresponding electric transport devices used to pair the user to the paired selected electric transport device based on the riding expertise of the user.

18. The method according to claim 15, wherein the riding expertise is at least one of experienced and expert and the paired selected electric transport device includes at least one of a short deck, advanced maneuverability, advanced speed, and a low handle bar.

* * * * *